United States Patent
O'Neil et al.

(10) Patent No.: US 7,811,276 B2
(45) Date of Patent: Oct. 12, 2010

(54) MEDICAL SENSOR AND TECHNIQUE FOR USING THE SAME

(75) Inventors: Michael P. O'Neil, Danville, CA (US); David B. Swedlow, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 0 days.

(21) Appl. No.: 12/389,746

(22) Filed: Feb. 20, 2009

(65) Prior Publication Data

US 2009/0156914 A1 Jun. 18, 2009

Related U.S. Application Data

(63) Continuation of application No. 11/441,583, filed on May 26, 2006, now abandoned.

(60) Provisional application No. 60/735,621, filed on Nov. 10, 2005.

(51) Int. Cl.
*A61M 31/00* (2006.01)

(52) U.S. Cl. ................ 604/504; 600/349; 600/309; 600/353

(58) Field of Classification Search ........... 600/309, 600/348, 349, 353, 357; 604/504, 77
See application file for complete search history.

(56) References Cited

U.S. PATENT DOCUMENTS

| | | | |
|---|---|---|---|
| 2,136,236 A | 11/1938 | Draper | |
| 2,638,096 A | 5/1953 | Waldhaus | |
| 2,880,072 A | 3/1959 | Grosskopf | |
| 2,890,177 A | 6/1959 | Kilmer | |
| 2,904,033 A | 9/1959 | Shane | |
| 3,067,015 A | 12/1962 | Lawdermilt | |
| 3,068,073 A | 12/1962 | Stanford | |
| 3,113,842 A | 12/1963 | Udall | |
| 3,114,610 A | 12/1963 | Gafford et al. | |
| 3,238,020 A | 3/1966 | Eiseman | |
| 3,363,833 A | 1/1968 | Laerdal | |
| 3,373,735 A | 3/1968 | Gallagher | |
| 3,420,635 A | 1/1969 | Davis | |
| 3,467,601 A | 9/1969 | Brauer | |
| 3,505,022 A | 4/1970 | Luckey | |

(Continued)

FOREIGN PATENT DOCUMENTS

EP 0481719 4/1992

(Continued)

OTHER PUBLICATIONS

J.A. Berman et al.; "The Einstein Carbon Dioxide Detector"; Anesthesiology, vol. 60, No. 6; pp. 613-614 (1984).

(Continued)

*Primary Examiner*—Kevin C Sirmons
*Assistant Examiner*—Deanna K Hall
(74) *Attorney, Agent, or Firm*—Fletcher Yoder

(57) ABSTRACT

A sensor is provided that is appropriate for transcutaneous detection of tissue or blood constituents. A sensor for tissue constituent detection may include a gas collection chamber with a conduit to a sensing component and a conduit from the sensing component to the chamber. A sensor as provided may also include a barrier layer to prevent water from infiltrating the sensor.

15 Claims, 6 Drawing Sheets

U.S. PATENT DOCUMENTS

| | | | |
|---|---|---|---|
| 3,507,623 A | | 4/1970 | McConnaughey |
| 3,556,122 A | | 1/1971 | Laerdal |
| 3,612,048 A | | 10/1971 | Takaoka et al. |
| 3,615,233 A | | 10/1971 | Doering et al. |
| 3,659,586 A | | 5/1972 | Johns et al. |
| 3,694,164 A | | 9/1972 | Guenther |
| 3,754,867 A | | 8/1973 | Guenther |
| 3,830,630 A | | 8/1974 | Kiefer et al. |
| 4,003,709 A | | 1/1977 | Eaton et al. |
| 4,005,700 A | * | 2/1977 | Parker .................. 600/364 |
| 4,019,862 A | | 4/1977 | Dahms |
| 4,077,404 A | | 3/1978 | Elam |
| 4,106,502 A | | 8/1978 | Wilson |
| 4,144,306 A | | 3/1979 | Figueras |
| 4,277,251 A | | 7/1981 | Leichnitz |
| 4,287,153 A | | 9/1981 | Towsend |
| 4,332,771 A | | 6/1982 | Leichnitz |
| 4,346,584 A | | 8/1982 | Boehringer |
| 4,366,821 A | | 1/1983 | Wittmaier et al. |
| 4,389,372 A | | 6/1983 | Lalin |
| 4,438,067 A | | 3/1984 | Siddiqi |
| 4,548,906 A | | 10/1985 | Sekikawa et al. |
| 4,557,900 A | | 12/1985 | Heitzmann |
| 4,557,901 A | | 12/1985 | Koyama et al. |
| 4,691,701 A | | 9/1987 | Williams |
| 4,728,499 A | | 3/1988 | Fehder |
| 4,734,125 A | | 3/1988 | Gehring et al. |
| 4,774,941 A | | 10/1988 | Cook |
| 4,780,411 A | | 10/1988 | Piejko et al. |
| 4,788,153 A | | 11/1988 | Detwiler et al. |
| 4,790,327 A | | 12/1988 | Despotis |
| 4,805,623 A | | 2/1989 | Jobsis et al. |
| 4,824,640 A | | 4/1989 | Hildenbrand et al. |
| 4,832,034 A | * | 5/1989 | Pizziconi et al. ........... 600/366 |
| 4,879,999 A | | 11/1989 | Leiman et al. |
| 4,890,619 A | | 1/1990 | Hatschek |
| 4,928,687 A | | 5/1990 | Lampotang et al. |
| 4,945,918 A | | 8/1990 | Abernathy |
| 4,994,117 A | | 2/1991 | Fehder |
| 4,999,306 A | | 3/1991 | Yafuso et al. |
| 5,005,572 A | | 4/1991 | Raemer et al. |
| 5,109,840 A | | 5/1992 | Daleiden |
| 5,124,129 A | | 6/1992 | Riccitelli et al. |
| 5,156,159 A | | 10/1992 | Lampotang et al. |
| 5,166,075 A | | 11/1992 | Fehder |
| 5,179,002 A | | 1/1993 | Fehder |
| 5,197,464 A | | 3/1993 | Babb et al. |
| 5,204,922 A | | 4/1993 | Weir et al. |
| 5,279,289 A | | 1/1994 | Kirk |
| 5,291,879 A | | 3/1994 | Babb et al. |
| 5,322,612 A | | 6/1994 | Abe et al. |
| 5,361,758 A | | 11/1994 | Hall et al. |
| 5,375,592 A | | 12/1994 | Kirk et al. |
| 5,456,249 A | | 10/1995 | Kirk |
| 5,468,451 A | | 11/1995 | Gedeon |
| 5,472,668 A | | 12/1995 | Mills et al. |
| 5,480,611 A | | 1/1996 | Mills et al. |
| 5,494,032 A | | 2/1996 | Robinson et al. |
| 5,517,985 A | | 5/1996 | Kirk et al. |
| 5,520,997 A | | 5/1996 | Pourahmady et al. |
| 5,634,426 A | | 6/1997 | Tomlinson et al. |
| 5,679,884 A | | 10/1997 | Kirk |
| 5,714,121 A | | 2/1998 | Alderete et al. |
| 5,743,259 A | * | 4/1998 | Kruse et al. ............... 600/309 |
| 5,749,358 A | | 5/1998 | Good et al. |
| 5,783,110 A | | 7/1998 | Verdicchio et al. |
| 5,846,836 A | | 12/1998 | Mallow |
| 5,849,594 A | | 12/1998 | Balderson et al. |
| 6,055,447 A | | 4/2000 | Weil et al. |
| 6,058,933 A | | 5/2000 | Good et al. |
| 6,123,075 A | | 9/2000 | Kirk |
| 6,216,024 B1 | | 4/2001 | Weil et al. |
| 6,265,221 B1 | | 7/2001 | Nilsson |
| 6,319,723 B1 | | 11/2001 | Jeffers et al. |
| 6,378,522 B1 | | 4/2002 | Pagan |
| 6,427,687 B1 | | 8/2002 | Kirk |
| 6,428,748 B1 | | 8/2002 | Wallach |
| 6,436,347 B1 | | 8/2002 | Cedeon |
| 6,502,573 B1 | | 1/2003 | Ratner |
| 6,576,474 B2 | | 6/2003 | Wallach |
| D478,522 S | | 8/2003 | Geist |
| 6,654,622 B1 | | 11/2003 | Eberhard et al. |
| 6,677,159 B1 | | 1/2004 | Mallow |
| 6,709,403 B1 | | 3/2004 | Ratner |
| 6,731,963 B2 | | 5/2004 | Finarov et al. |
| 6,802,812 B1 | | 10/2004 | Walker et al. |
| 6,816,266 B2 | | 11/2004 | Varshneya et al. |
| 6,929,008 B2 | | 8/2005 | Geist |
| 6,934,571 B2 | | 8/2005 | Wiesmann et al. |
| 7,024,235 B2 | | 4/2006 | Melker et al. |
| 7,127,278 B2 | | 10/2006 | Melker et al. |
| 7,319,894 B2 | | 1/2008 | Higgins et al. |
| 7,341,560 B2 | | 3/2008 | Henderson et al. |
| 7,392,074 B2 | | 6/2008 | Isaacson et al. |
| 7,440,788 B2 | | 10/2008 | Jenkins et al. |
| 2002/0128544 A1 | | 9/2002 | Diab et al. |
| 2003/0003593 A1 | | 1/2003 | Wallach |
| 2003/0133123 A1 | | 7/2003 | Yeh |
| 2003/0199095 A1 | | 10/2003 | Yuyama et al. |
| 2004/0065329 A1 | | 4/2004 | Geist |
| 2004/0184024 A1 | | 9/2004 | Katura et al. |
| 2004/0230108 A1 | | 11/2004 | Melker et al. |
| 2004/0260161 A1 | | 12/2004 | Melker et al. |
| 2005/0016543 A1 | | 1/2005 | Geist |
| 2005/0039751 A1 | | 2/2005 | Pagan |
| 2005/0049468 A1 | | 3/2005 | Carlson et al. |
| 2005/0059869 A1 | | 3/2005 | Scharf et al. |
| 2005/0113704 A1 | | 5/2005 | Lawson et al. |
| 2006/0020179 A1 | | 1/2006 | Anderson et al. |
| 2006/0167351 A1 | | 7/2006 | Isaacson et al. |
| 2007/0060809 A1 | | 3/2007 | Higgins et al. |
| 2007/0078318 A1 | | 4/2007 | Kling et al. |
| 2008/0108887 A1 | | 5/2008 | Higgins et al. |
| 2008/0139908 A1 | | 6/2008 | Kurth |
| 2008/0262328 A1 | | 10/2008 | Adams |

FOREIGN PATENT DOCUMENTS

| | | |
|---|---|---|
| EP | 0307625 | 4/1994 |
| EP | 0257916 | 1/1995 |
| EP | 0509998 | 1/1996 |
| EP | 0451719 | 12/1996 |
| EP | 0601171 | 9/1997 |
| EP | 1022558 | 7/2000 |
| EP | 01022558 | 7/2000 |
| EP | 1039294 | 9/2000 |
| EP | 630203 | 7/2002 |
| EP | 1245947 | 10/2002 |
| EP | 1266944 | 12/2002 |
| EP | 0858594 | 4/2003 |
| EP | 1327874 | 7/2003 |
| EP | 0943093 | 11/2003 |
| EP | 1491135 | 12/2004 |
| JP | 07072081 | 3/1995 |
| JP | 08145979 | 6/1996 |
| JP | 08247997 | 9/1996 |
| JP | 09318528 | 12/1997 |
| JP | 10073560 | 3/1998 |
| JP | 2003072857 | 3/2003 |
| JP | 2004177247 | 6/2004 |
| JP | 2005054048 | 3/2005 |
| WO | WO9001695 | 2/1990 |
| WO | WO9003819 | 4/1990 |
| WO | WO9105252 | 4/1991 |

| WO | WO9220404 | 11/1992 |
| WO | WO9316629 | 9/1993 |
| WO | WO9320431 | 10/1993 |
| WO | WO9400756 | 1/1994 |
| WO | WO9619727 | 6/1996 |
| WO | WO9624054 | 8/1996 |
| WO | WO9710496 | 3/1997 |
| WO | WO9712227 | 4/1997 |
| WO | WO9817174 | 4/1998 |
| WO | WO9826283 | 6/1998 |
| WO | WO0029830 | 5/2000 |
| WO | WO0043778 | 7/2000 |
| WO | WO0104624 | 1/2001 |
| WO | WO0144385 | 6/2001 |
| WO | WO03045608 | 3/2003 |
| WO | WO2004077035 | 9/2004 |
| WO | WO2006124696 | 11/2006 |
| WO | WO2007013054 | 2/2007 |
| WO | WO2007041331 | 4/2007 |

OTHER PUBLICATIONS

P.K. Birmingham et al.; "Esophageal Intubation: A Review of Detection Techniques"; Anesth. Analg.; vol. 65; pp. 886-891 (1986).

Current Projects CapnoProbe™ SL Monitoring System posted on the company's web site; Optical Sensors Incorporated | Projects . . . http://64.226.16.15/projects.htm Copyright 2003.

S.G.R.G. Barton et al.; "Expression of heat shock protein 32 (hemoxygenase-1) in the normal and inflamed human stomach and colon: an immunohistochemical study"; Cell Stress & Chaperones, vol. 8, No. 4; pp. 329-334 (2003).

Jessy Deshane et al.; "Heme oxygenase-1 expression in disease states"; Acta Biochimica Polonica, vol. 52, No. 2; pp. 273-284 (2005).

Shai Efrati, MD et al.; "Optimization of Endotracheal Tube Cuff Filling by Continuous Upper Airway Carbon Dioxide Monitoring"; Anesth. Analg; vol. 101, pp. 1081-1088 (2005).

Shai Efrati, MD; "Is Capnometry the Optimum Method for Assessing the Adequacy of Endotracheal Tube Cuff Seal?"; Anesthesia & Analgesia; vol. 103, No. 2; pp. 505-506 (Aug. 2006).

Shaw-Fang Yet et al.; "Heme Oxygenase 1 in Regulation of Inflammation and Oxidative Damage"; Methods in Enzymology; vol. 353, pp. 163-176 (2002).

* cited by examiner

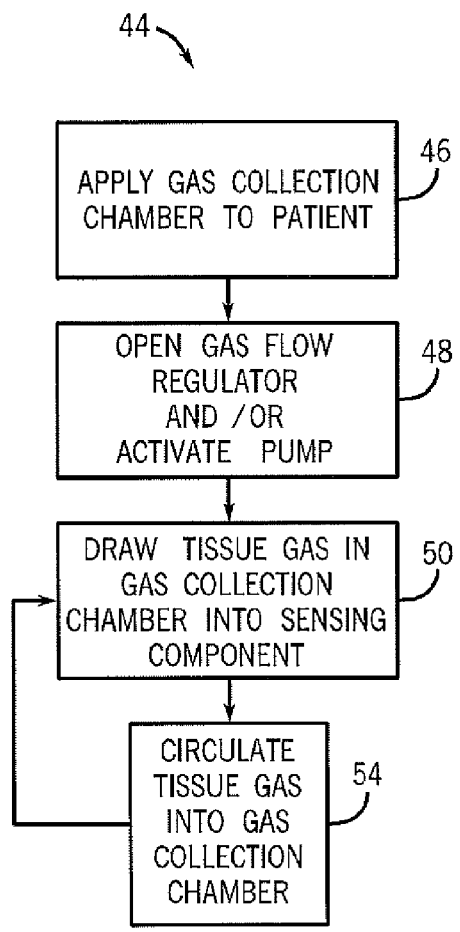
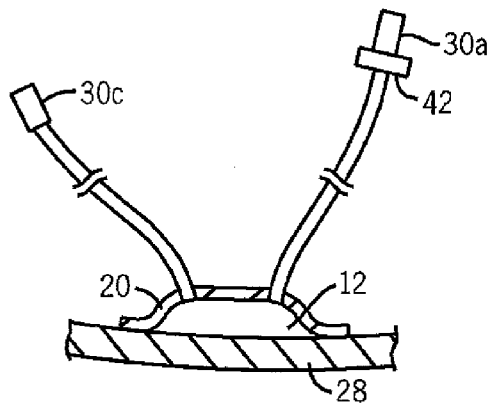
FIG. 3B
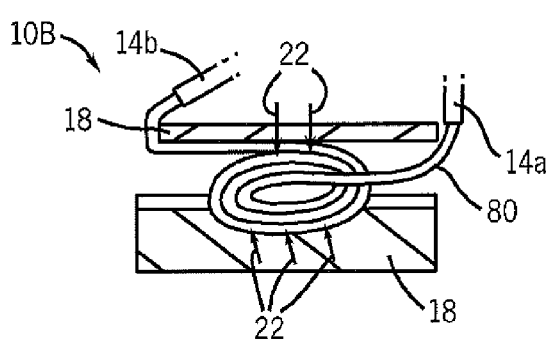
FIG. 5A
FIG. 4
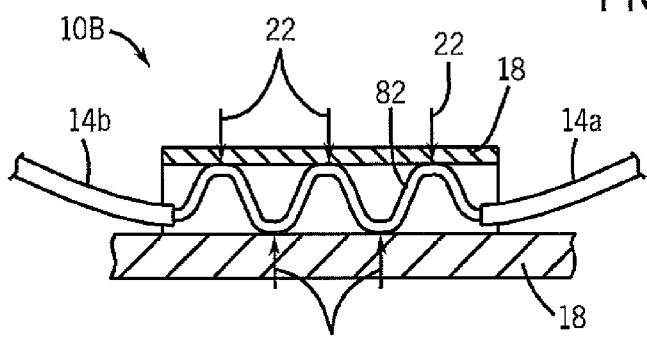
FIG. 5B

MEDICAL SENSOR AND TECHNIQUE FOR USING THE SAME

CROSS-REFERENCE TO RELATED APPLICATIONS

This application is a continuation of U.S. application Ser. No. 11/441,583, filed May 26, 2006, which claims priority to U.S. Provisional Application No. 60/735,621, filed Nov. 10, 2005, the disclosures of which are hereby incorporated by reference in their entirety for all purposes.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

Physiological characteristics that physicians may desire to monitor include constituents of the blood and tissue, such as oxygen and carbon dioxide. For example, abnormal levels of carbon dioxide in the blood may be related to perfusion problems. Thus, assessment of carbon dioxide levels may be useful for diagnosing a variety of clinical states related to the circulation. Carbon dioxide and other blood constituents may be directly measured by taking a blood sample, or may be indirectly measured by assessing the concentration of those constituents in the tissue or respiratory gases. For example, carbon dioxide in the bloodstream equilibrates rapidly with carbon dioxide in the lungs, and the partial pressure of the carbon dioxide in the lungs approaches the amount in the blood during each breath. Accordingly, physicians often monitor respiratory gases during breathing in order to estimate the carbon dioxide levels in the blood.

However, estimation of carbon dioxide by respiratory gas analysis has certain disadvantages. It is often inconvenient to measure carbon dioxide in samples collected from an intubation tube or cannula. Although these methods are considered to be noninvasive, as the surface of the skin is not breached, the insertion of such devices may cause discomfort for the patient. Further, the insertion and operation of such devices also involves the assistance of skilled medical personnel.

Carbon dioxide in the blood that diffuses into the tissue may also be measured transcutaneously by sensors placed against a patient's skin. While these sensors are easier to use than respiratory gas sensors, they also have certain disadvantages. For example, these sensors may be sensitive to the infiltration of water or bodily fluids, particularly when applied to a mucosal surface.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a system that includes: at least one gas collection chamber into which a tissue constituent is able to diffuse, wherein the gas collection chamber is adapted to be placed proximate to a tissue; an efferent conduit adapted to transfer the tissue constituent from the gas collection chamber to at least one sensing component, wherein the sensing component is adapted to provide a signal related to the tissue constituent; an afferent conduit adapted to transfer the tissue constituent from the sensing component to the gas collection chamber; and a motive force structure adapted circulate the tissue constituent through the system, wherein the motive force structure is adapted to be operatively connected to at least one of the efferent conduit, the afferent conduit, or the sensing component.

There is also provided a monitoring device that includes: a monitor; and a system adapted to be coupled to the monitor, the system including: at least one gas collection structure adapted to be placed proximate to a tissue; and an efferent conduit adapted to transfer gas from the gas collection structure to a sensing component, wherein the sensing component is adapted to provide a signal related to a tissue constituent; and an afferent conduit adapted to transfer gas from the sensing component to the gas collection structure.

There is also provided a method that includes: transferring a tissue constituent in a gas collection chamber to at least one sensing component not located in the gas collection chamber, wherein the sensing component is adapted to provide a signal related to the tissue constituent.

There is also provided a sensing system component that includes: at least one gas collection chamber into which a tissue constituent is able to diffuse, wherein the gas collection chamber is adapted to be placed proximate to a tissue; a first conduit in communication with the gas collection chamber comprising a connector located distally from the gas collection; and a second conduit in communication with the gas collection chamber comprising a connector located distally from the gas collection chamber.

There is also provided a method of manufacturing a sensing system component that includes: providing at least one gas collection chamber into which a tissue constituent is able to diffuse, wherein the gas collection chamber is adapted to be placed proximate to a tissue; providing a first conduit in communication with the gas collection chamber comprising a connector located distally from the gas collection; and providing a second conduit in communication with the gas collection chamber comprising a connector located distally from the gas collection chamber.

There is also provided a sensor that includes: a sensor body comprising at least one gas collection chamber adapted to be placed proximate to a tissue; a sensing component disposed on the sensor body adapted to provide a signal related to a tissue constituent; and a barrier layer defining at least part of a surface of the gas collection chamber, wherein the barrier layer is substantially impermeable to water.

There is also provided a system that includes: a monitor; and a sensor adapted to be coupled to the monitor, the sensor including: a sensor body comprising a gas collection chamber adapted to be placed proximate to a tissue; a sensing component disposed on the sensor body adapted to provide a signal to the monitor related to a tissue constituent; and a barrier layer defining at least part of a surface of the gas collection chamber, wherein the barrier layer is substantially impermeable to water.

There is also provided a method of measuring a tissue constituent that includes: diffusing a tissue constituent though a barrier layer that is substantially impermeable to water, wherein the barrier layer defines at least part of a surface of a gas collection chamber; and providing a signal related to the tissue constituent with a sensing element disposed on the gas collection chamber.

There is also provided a method of manufacturing a sensor that includes: providing a sensor body comprising a gas collection chamber adapted to be placed proximate to a tissue; providing a sensing component disposed on the sensor body adapted to provide a signal related to a tissue constituent; and providing a barrier layer defining at least part of a surface of the gas collection chamber, wherein the barrier layer is substantially impermeable to water.

BRIEF DESCRIPTION OF THE DRAWINGS

Advantages of the invention may become apparent upon reading the following detailed description and upon reference to the drawings in which:

FIG. 3B illustrates a view of an exemplary disposable portion of the sensor of FIG. 3A;

FIG. 4 is a flow chart of a method of operating a sensor according to the present invention;

FIGS. 5A-5B illustrate an alternate configuration of a tissue constituent collection portion of a sensor according to the present techniques;

DETAILED DESCRIPTION OF SPECIFIC EMBODIMENTS

Figure 1:
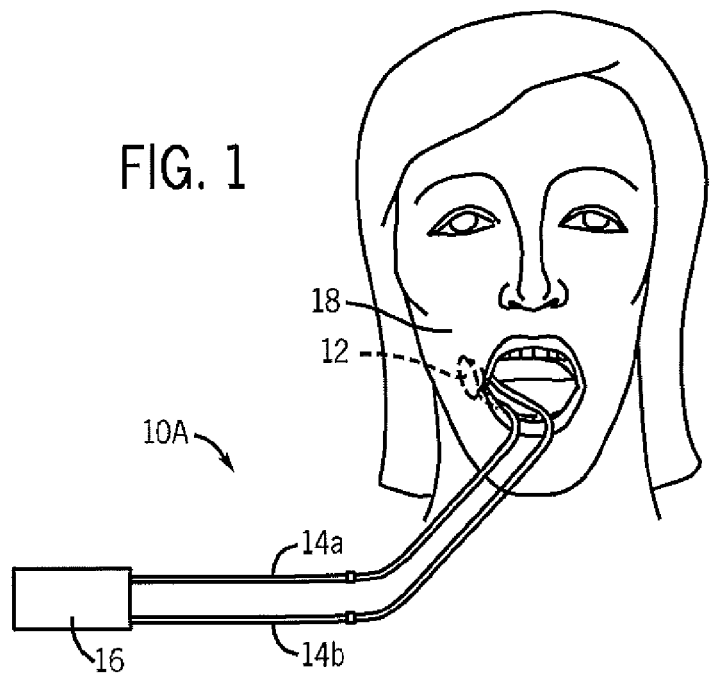
FIG. 1 illustrates a perspective view of a patient using a sensor for detection of a physiological tissue constituent according to the present invention.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A sensor and/or sensing system is provided herein that may assess a tissue constituent content with a sensing component that is adapted to provide a signal related to the tissue constituent. In certain embodiments of the invention, the sensing system may include a collection chamber placed against the tissue and a sensing component that is connected to the chamber by a conduit with a return conduit between the sensing component and the collection chamber. The collection chamber is able to capture a volume of volatile tissue constituents as they diffuse out of the tissue. When the concentration of the tissue constituents in the gas collection chamber and throughout the sensing system is substantially equal to the concentration of those constituents in the tissue, the sensing system is equilibrated Such a system may provide multiple advantages. By separating the sensing component from the tissue constituent collection chamber, a sensor may be more versatile. For example, a sensing component may be easily exchanged for an alternate sensing component without disrupting the collection of the tissue constituent. This may be advantageous when a sensing component needs to be maintained or serviced, and the healthcare provider does not wish to disrupt physiological monitoring while replacing the sensing component. Additionally, the separation of the sensing component from the tissue constituent collection chamber may help reduce water infiltration into the sensing component.

Sensors according to the present techniques may transcutaneously sense tissue gases or other tissue constituents in a tissue layer and provide an electrical and/or visual signal. For example, carbon dioxide and other constituents in the bloodstream may diffuse through the tissue and may dissolve into any liquids that may be found at the surface of the tissue. Thus, the levels of carbon dioxide in the tissue may serve as a surrogate marker for carbon dioxide levels in the bloodstream. A sensor according to the present techniques placed proximate to a tissue surface may capture and measure carbon dioxide that would otherwise diffuse into the airstream or other surrounding airspace.

Generally, it is envisioned that sensors according to the present techniques are appropriate for use in determining the presence or levels of tissue constituents in a variety of tissues. The sensor may be placed against the tissue, either manually, mechanically, adhesively, or otherwise, forming a seal to prevent the carbon dioxide from diffusing away. For example, a sensor may be used in the upper respiratory tract or the gastrointestinal tissue, including the oral and nasal passages. These passages may include the tongue, the floor of the mouth, the roof of the mouth, the soft palate, the cheeks, the gums, the lips, the esophagus and any other respiratory or gastrointestinal tissue. Further, a sensor as described herein is appropriate for use adjacent to or proximate to any mucosal surface, i.e., patient surfaces that include a mucous membrane or surfaces that are associated with mucus production. In addition to the respiratory tract, mucosal surfaces may include vaginal, rectal, or gastrointestinal surfaces.

Sensors as provided by the present techniques may be disposable, reusable, or partially disposable. In addition, the sensors may be appropriate for short-term or for longer-term monitoring. When used for long-term monitoring, the sensor may be applied to the patient's tissue either by mechanical clamping or by a suitable adhesive, such as a mucoadhesive, or by any other suitable holding device, such as a clip.

In additional to carbon dioxide monitoring, sensors and sensing systems as provided herein may be used to monitor oxygen, carbon monoxide, ethanol, or anesthetic gases (such as isoflurane, halothane, desflurane, sevoflurane and enflurane) that may diffuse transcutaneously. Additionally, these sensors and/or sensing systems may be used to monitor volatile products of metabolism (such as ketones, alcohols, lactones, terpenes, furans, dimethyl sulfone, pyrrole, and allyl isothiocyanate), as well as volatile xenobiotics and their metabolites. Further, these sensors may be useful in monitoring the levels of parenterally administered or enterally administered therapeutic agents.

For example, FIG. 1 illustrates the placement of a gas collection chamber 12 of a sensor 10 on a buccal surface in order to assess a tissue gas, for example carbon dioxide, in the tissue, blood or interstitial fluid. Specifically, FIG. 1 shows an embodiment of a sensor 10 including a gas collection chamber 12 and a conduit 14 in communication with a sensing component 16. The conduit 14 may be adapted to transport gases from the gas collection chamber 12 to a distal sensing component 16. The collected gases may diffuse through the efferent conduit 14a that is connected to the collection chamber, and the gases may then be further assessed and/or measured by the sensing component 16, discussed in more detail below. The collected gases may then circulate back to the gas collection chamber 12 through the afferent conduit 14b. The gas collection chamber 12 may be suitably sized and shaped such that a patient may easily close his or her mouth around the sensor with minimal discomfort.

The gas collection chamber 12 is secured to the mucosal tissue 18 such that the area covered by the gas collection chamber 12 creates a seal 13 to prevent environmental air flow out or into of the gas collection chamber 12, thus preventing tissue gases at the gas collection chamber 12 placement site from dissipating into the airstream or being diluted, which may lead to inaccurate measurements. Further, the gas collection chamber's 12 tissue seal may also prevent respiratory gases or oral fluids from entering the sensor 10A.

Tissue constituents 22 may be transferred through a conduit 14, which may include tubes or tube segments. The conduit 14 may include, for example, medical grade catheter tubing, polyethylene, polypropylene or vinyl. The efferent conduit 14a and the afferent conduit 14b may be disposed on any appropriate location on the gas collection chamber 12. For example, the efferent conduit 14a and the afferent conduit 14b may be parallel or perpendicular to each other. Generally, the conduit 14 may be relatively impermeable to the tissue constituent. This may be accomplished by selecting a conduit 14 made from an appropriate material or by applying a sealing coat to the conduit 14. The conduit 14 may include gas-impermeable plastics such as PET. Appropriate gas-impermeable coatings may include Funcosil® (available from Remmers, Loeningen, Germany). Such coatings may be applied to the conduit 14 in any appropriate manner.

Figure 2:
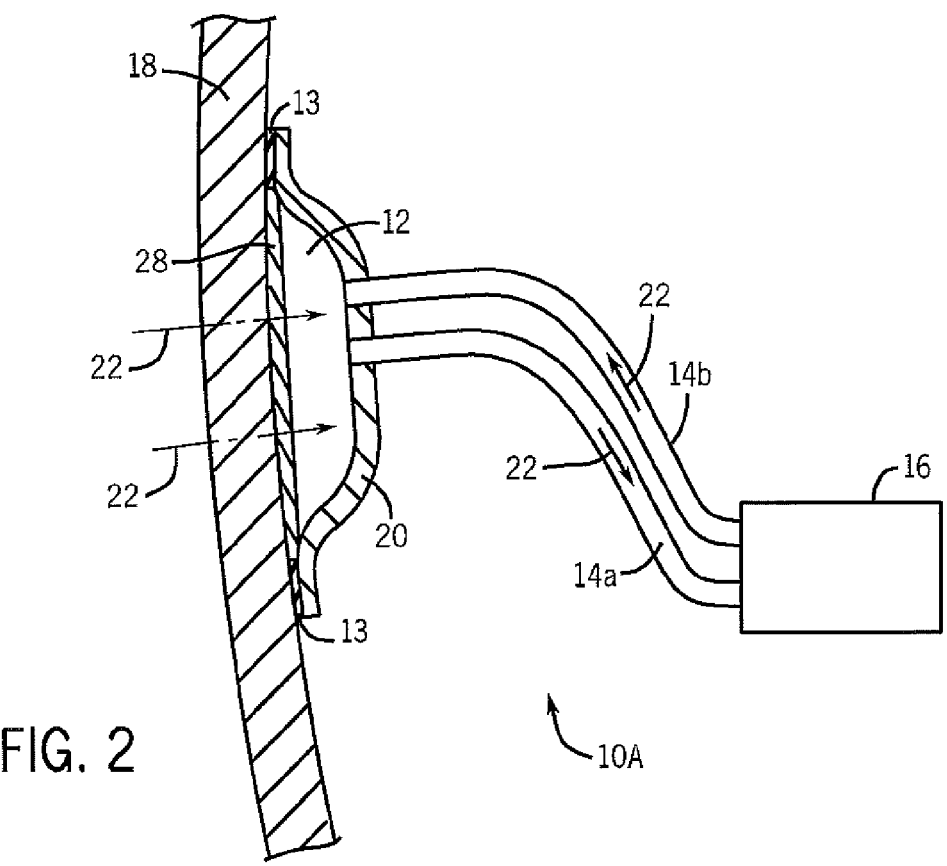
FIG. 2 is a schematic cross-sectional view of the sensor of FIG. 1.

A cross-sectional view of the sensor 10A is shown in FIG. 2. The housing 20 is formed to provide a surface that is suitably shaped to be secured against a mucosal tissue 18. The housing 20 may be any suitable material that is generally suited to the aqueous environment of the mucous membrane. For example, the housing 20 may be formed from polypropylene, polyethylene, polysulfone or similar polymers. Generally, the housing 20 should be substantially impermeable to tissue constituents, shown by arrows 22, such that the sensor 10A may collect tissue constituents 22, such as tissue gases, for a sufficient period of time to allow for detection and measurement. Hence, it may be advantageous to coat the sensor 10A with additional sealants to prevent leakage of the tissue constituents 22. The housing 20, once secured to the tissue, forms a collection chamber 12 that traps tissue constituents 22 that diffuse through the mucosal tissue 18. The trapped tissue gas 22 may then be transferred to the sensing component 16, which is coupled the gas collection chamber 12 by the efferent conduit 14a.

In the depicted embodiment, the sensing component 16 is not located on or within the gas collection chamber 12. When the housing 20 is contacted with a tissue sensor site, blood or tissue constituents 22 perfuse through the tissue and enter the collection chamber 12. The sensing component 16 is adapted to respond to the presence of the blood or tissue constituents 22 collected in the gas collection chamber 12 and to provide a signal, as discussed in more detail below. The sensing component 16 is sensitive to the presence of a tissue constituent 22 and may be capable of being calibrated to give a response signal corresponding to a given predetermined concentration of the tissue constituent. In certain embodiments, the signal may be related to the concentration or level of the tissue constituent 22, or the partial pressure of the tissue constituent 22.

In certain embodiments, the gas collection chamber 12 may include materials that function as a barrier layer 28 that are hydrophobic or otherwise water-resistant, but that are permeable to carbon dioxide. For example, a barrier layer 28 may form a contact surface of the sensor 10A that prevents water from entering the sensor 10A. In such an embodiment, carbon dioxide in the tissue can perfuse through the contact surface to enter the gas collection chamber 12. In one embodiment, it is envisioned that the ratio of water permeability to carbon dioxide permeability of a barrier layer 28 may be less than 1:1, and in certain embodiments, the ratio may be less than 1:10. Suitable materials include polymers, such as polytetrafluorethylene (PTFE). Other suitable materials include microporous polymer films, such as those available from the Landec Corporation (Menlo Park, Calif.). Such microporous polymer films are formed from a polymer film base with a customizable crystalline polymeric coating that may be customized to be highly permeable to carbon dioxide and relatively impermeable to water. In one embodiment, the barrier layer 28 may be a relatively thin PTFE material such as plumber's tape (0.04 mm). In other embodiments, the barrier layer 28 may be a PTFE material such as Gore-Tex® (W. L. Gore & Associates, Inc., Newark, Del.) or plumber's tape. Alternatively, the barrier layer 28 may be formed from a combination of appropriate materials, such as materials that are heat-sealed or laminated to one another. For example, the barrier layer 28 may include a PTFE layer with a pore size of 3 microns and a second PTFE layer with a pore size of 0.1 microns. Additionally, in certain embodiments, a sensor 10A may also include a porous substrate 29 that is permeable to a wide variety of tissue constituents 22. As a barrier layer 28 may be quite thin, the porous substrate may be advantageous in providing rigidity and support to the barrier layer 28 film. The porous substrate may be adhered, laminated, or otherwise attached to the barrier layer 28. In certain embodiments, the porous substrate may be disposed on the tissue-contacting side of the barrier layer 28. Suitable materials for the porous substrate include paper, plastics, or woven materials.

In certain embodiments, the barrier layer 28 or porous substrate 29 may include a tissue irritant or other agent or structure that increases blood flow to the tissue at the gas collection chamber 12 placement site. The agent may include a counterirritant, such as a mixture of methyl salicilate and menthol (12% methyl salicilate, 9% menthol) in a cream base is applied to the patient's skin at the chosen sensor site. A cream of this type is sold in retail drug stores under the trademark ICY HOT. Other contemplated agents of this type may include heaters, such as mechanical or chemical heaters, that increase blood perfusion in response to lowered tissue temperatures.

The sensing component 16 may be disposed on or within any appropriate substrate that provides a suitable contact area with which the tissue constituent 22 may interact, react, or otherwise come into the proximity of the sensing component 16. For example, in embodiments in which the sensing component includes a chemical indicator, it may be appropriate to include, as part of a holder for the sensing component 16, a transparent viewing window for the healthcare provider to view a change in color of the indicator. In embodiments in which the sensing component includes an optical detection system, it may be appropriate to dispose the sensing component in a chamber.

Figure 3A:
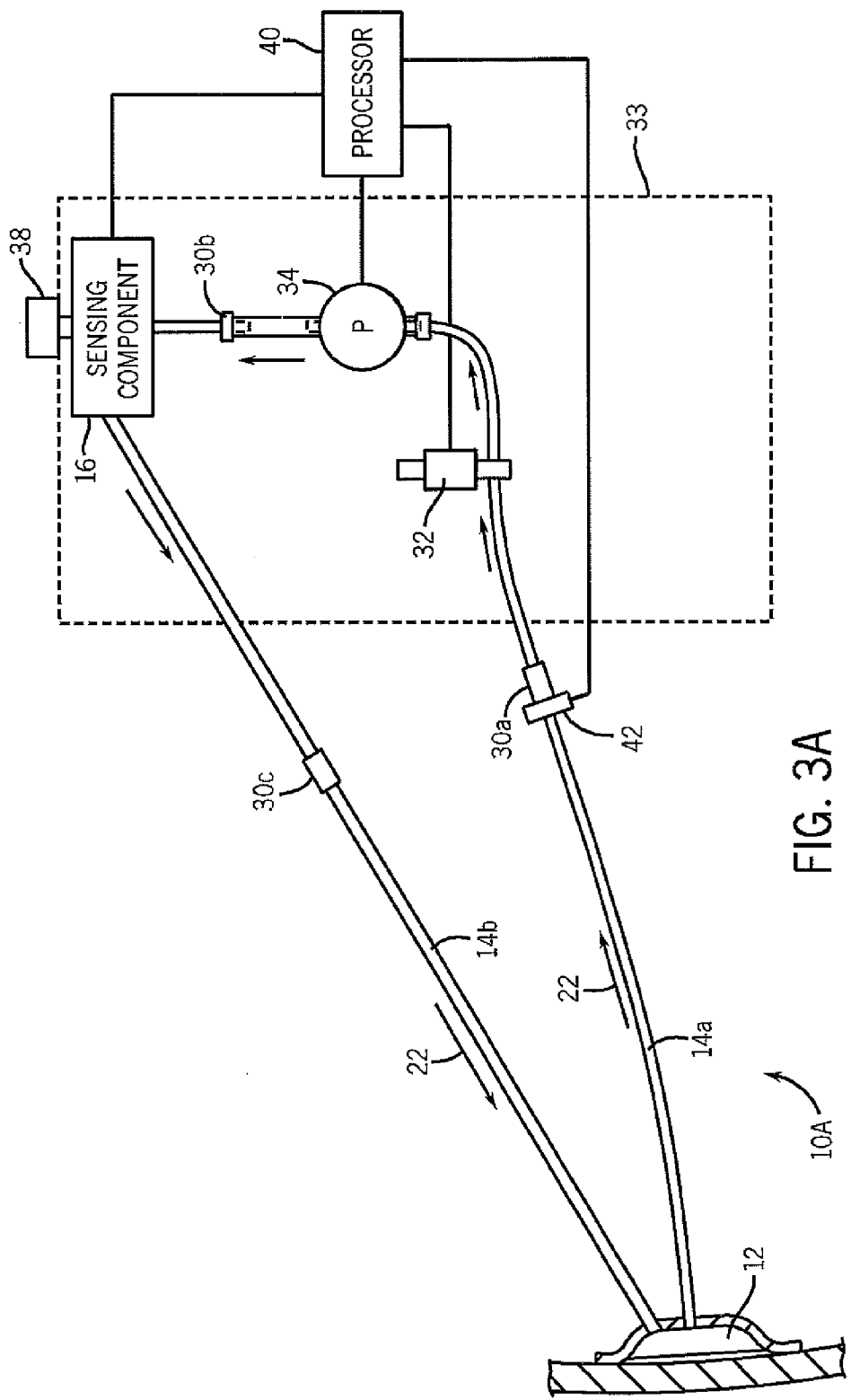
FIG. 3A illustrates a schematic view of an embodiment of a sensor according to the present techniques.

Although the tissue constituent 22 may diffuse and circulate through the conduit 14 to the sensing component 16 without a drawing force, such a process may be lengthy. Thus, it may be advantageous to provide a motive device, such as a pump, within the sensor. FIG. 3 is a schematic diagram of the exemplary sensor 10A that provides a pumping and sensing component system 33 to draw the tissue constituent 22 to the sensing component 16. A flow regulator 32, which may be a valve or any other suitable device, and pump 34 are connected into or between segments of conduit 14 to maintain a desired flow velocity of the stream of tissue constituent 22 to the sensing component 16. As shown, the flow regulator 32 is connected to a pump 34. The pump 34 is in turn interposed between sections of the conduit 14, which is connected to the sensing component 16.

The ends of the conduit 14 segments may be secured to connectors 30, as shown in FIG. 3, which may be clamped to prevent leaking of the tissue constituent 22 to the outside. Connectors 30a and 30b are exemplary, and it should be understood that the connectors 30 and conduit 14 may be arranged along the sensor in any manner that is convenient for the user. For example, it may be advantageous to provide additional connectors 30 in order to allow a healthcare provider to easily swap out to service, clean, or exchange any part of the sensor 10A, including the flow regulator 32, pump, 34, or sensing component 16.

In certain embodiments, it may be advantageous to exchange a first sensing component 16 adapted to sense carbon dioxide for a second sensing component 16. The second sensing component 16 may also sense carbon dioxide, but may operate by a different sensing mechanism. Alternatively, the second sensing component 16 may be adapted to sense a different tissue constituent, such as carbon monoxide or oxygen. Further, in an alternate embodiment (not shown), the sensor 10A may have multiple sensing components 16 in series.

In certain embodiments, the pump 34 and flow regulator 32 may be adjusted so that the flow is maintained at the desired rate. One suitable flow regulator is orifice/needle valve model F-2822-41-B80-55 available from Air Logic, Racine, Wis., which can be adjusted to obtain a desired gas flow rate in the range of up to 40-60 ml/min. One suitable pump is model NMP 05 diaphragm micro pump, available from KNF Neuberger, Inc, Princeton, N.J., which has a free flow capacity of 0.4 ml/min. The pump 34 and flow regulator 32 may be located anywhere in the flow stream of the sensor 10A. Generally, the pumping system is substantially sealed to prevent leaking of the tissue constituent 22 to the outside or dilution by entraining of fresh gas. In other embodiments, any suitable motive force structure may be appropriate for use with the present techniques. For example, suitable motive force structures include gravity pumps, one-way valves, kinetic motion pumps, or piezoelectric pumps.

In certain embodiments, the pump 34, flow regulator 32, and sensing component 16 may be connected to a processor 40. The processor may be part of a monitor or multi-parameter monitor, as discussed in detail below. The processor 40 may receive signals related to the output signals from sensing component 16, corresponding to the tissue constituent 22 concentration or partial pressure concentration. Additionally, the processor 40 may control the flow of the vacuum and sensing component system 33. It should be understood that the processor 40 may be adapted to determine a suitable equilibration time of the sensor 10A by comparing the equilibration time to stored equilibration curves that may be empirically obtained. Additionally, in certain embodiments, the concentration of the tissue constituent 22 may be extrapolated from a concentration curve obtained by the sensor 10A during the pre-equilibration period, as such a curve will start to plateau as it approaches the equilibrated state.

In certain embodiments, the gas collection chamber 12, the conduit 14, or the connectors 30 may include a calibration element 42, such as a coded resistor or EEPROM or other coding devices (such as a capacitor, inductor, PROM, RFID, a barcode, parallel resonant circuits, or a colorimetric indicator) that may provide a signal to the processor 40 related to the volume and other characteristics of the gas collection chamber 12 that may allow the processor 40 to determine the appropriate calibration characteristics for the sensor 10A. Generally, such a calibration element 42 may be located on a disposable portion of the sensor 10A, shown in FIG. 3B, that may include the gas collection chamber 12, the conduit segments 14 attached to the gas collection chamber 12, or any connectors 30 proximate to the gas collection chamber 12. In such an embodiment, for example when the calibration element is disposed on the connector 30 as shown, the connector 30, conduit segment 14, and the calibration element 42 may be constructed as a unitary assembly such that the calibration element 42 may be inseparable from the gas collection chamber 12. Further, the calibration element 42 may include encryption coding that prevents a disposable part of the sensor 10A from being recognized by a processor 40 that is not able to decode the encryption. Such encryption coding is described in U.S. Pat. No. 6,708,049, which is hereby incorporated by reference in its entirety.

The sensing component 16 may also include a calibration element (not shown) that provides information to the processor 40 that may include the type of tissue constituent 22 that is being analyzed or other characteristics of the sensing component 16. For example, such a sensing component 16 calibration element may send a signal to the processor 40 to employ a certain correction algorithm for calculating the concentration of the tissue constituent 22. Such a correction algorithm may be appropriate when the sensing component 16 includes a chemical indicator that consumes a percentage of the tissue constituent 22 while actively measuring it. As the consumption of the tissue constituent 22 by the sensing component 16 may alter the equilibration state of the sensor 10A, the correction algorithm may mitigate such effects on the sensing component 16 output signal. In an alternative embodiment, a correction algorithm may also be employed if a sensing component 16 generated the tissue constituent 22 during measurement. Further, a correction algorithm may account for any minimal leakage of tissue constituent 22 in the system.

The collection chamber 12 is part of a substantially closed environment, as the conduit 14, and the sensing component 16 are generally impermeable to the tissue constituent 22 of interest. The sensor 10A is permeable to the tissue constituent 22 where the collection chamber 12 contacts the tissue 18. When the partial pressure of the tissue constituent 22 in the sensor 10A is substantially equal to the partial pressure of the tissue constituent in the tissue 18, the sensor 10A is equilibrated. The sensor 10A is arranged to provide circulating flow of the tissue constituent 22 through the sensor 10A. Thus, the tissue constituent 22 may equilibrate throughout the sensor 10A while being transferred from the gas collection chamber 12 through the efferent conduit 14a to contact the sensing component 16, and may return to the gas collection chamber 12 through the afferent conduit 14b. Such an embodiment may be advantageous when a tissue constituent 22 is being continuously or regularly monitored. As the initial application of the gas collection chamber 12 to the mucosal tissue 26 may involve waiting for 5-10 minutes before the tissue constituent 22 equilibrates in the gas collection chamber prior to being analyzed, it is desirable to keep the sensor in the equilibrated state. In such an embodiment, the vent 38 to the outside may be closed during equilibration and tissue constituent 22 monitoring. The vent 38 may be opened when necessary in order to flush out the sensor with room air or purge gas.

The equilibration time of the sensor 10A may be influenced by certain factors. Generally, equilibration times may be in the range of substantially instantaneous, i.e. real time, to less than 5 minutes. In certain embodiments, the response time is in the range of 5 seconds to 30 minutes. For example, in certain embodiments, the thickness of a barrier layer 28 may be modified in order to achieve the desired rate of carbon dioxide perfusion and sensing component 16 response time. Where a very rapid response is desired, a thin film of the barrier layer 28, for example less than 0.2 mm in thickness, may be used. Additionally, the barrier layer 28 may be formed with small pores that increase the carbon dioxide permeability. In other embodiments, the response time may be influenced by the volume of the gas collection chamber 12 or the length and diameter of the conduit 14. It is envisioned that the volume of the gas collection chamber 12 may be optimized to be large enough to allow sufficient tissue constituents 22 to be collected to obtain accurate measurements while being small enough to provide rapid response times. For example, in certain embodiments, the total volume of the gas collection chamber may be 0.2-5.0 cubic centimeters. It may be appropriate to use a relatively smaller, e.g., 0.2-0.8 cubic centimeters, gas collection chamber on a neonate. In certain embodiments, the total volume of the sensor 10A, including the conduit 14, sensing component 16, and pumping system 33 may be 2-500 cubic centimeters. Generally, smaller sensor 10A volumes are associated with faster equilibration times.

Referring to FIG. 4, a flow chart 44 illustrates how a tissue constituent 22 may be analyzed by the sensor 10A. A gas collection chamber 12 is applied to a patient's mucosal tissue (block 46) and the tissue constituent 22 diffuses into the gas collection chamber 12. The pump 34 and/or flow regulator 32 is then activated, either by the healthcare provider or by a processor 40 (block 49 and the tissue constituent 22 equilibrates while being pumped through the sensor 10A. The tissue constituent 22 is drawn into proximity with sensing component 16, and the sensing component 16 provides a signal related to the tissue constituent 22 (block 50). The tissue constituent 22 may be circulated through the sensor (block 54) back to the gas collection chamber 12 in order to maintain the equilibrated state.

In certain embodiments, it may be advantageous to provide a sensor with a gas collection portion with a large surface area that contacts the tissue. Such a sensor may equilibrate more rapidly, as tissue constituent 22 may diffuse more rapidly into the gas collection portion. FIGS. 5A-5B illustrate sensors 10B with alternative gas collection configurations. In FIG. 5A, a sensor 10B may include a gas collection portion in the form of a coiled tube 80, which may be coiled in the manner of a garden hose, that is permeable to the tissue constituent 22. The coiled tube 80 may increase the available surface area of the gas collection portion of the sensor 10B, as it may be adapted to lay flat against a tissue 18. The tissue constituent 22 diffuses into the coiled tube 80 and is drawn into the efferent conduit 14a. The tissue constituent 22 may be circulated through conduit 14b. Although the coiled tube 80 is permeable to the tissue constituent 22, the tissue constituent is able to equilibrate in the sensor as the coiled tube 80 may adapted to be substantially surrounded by mucosal tissue 18. For example, the coiled tube 80 may be placed sublingually. In an alternate embodiment, the coiled tube 80 may be adapted to be permeable only on one side by applying a tissue constituent impermeable coating (not shown) to certain portions of the coiled tube 80. Thus, once the tissue constituent 22 diffuses into the coiled tube 80, the partial pressure of the tissue constituent 22 in the sensor 10B may equilibrate with the tissue 18 without leaking out the portion of the coiled tube 80 not in contact with the tissue 18. Such a configuration may be appropriate for use on buccal tissue. In an alternate embodiment, shown in FIG. 5B, the tissue constituent permeable collection portion may assume a zigzag configuration 82 connected to the conduit 14. Exposed portion of the substrate 84, i.e., portions not in contact with the tissue 18, may be coated with a tissue constituent impermeable coating 86 to prevent leaking. It should be understood that the configurations shown are merely exemplary, and the gas collection portions of the sensor 10B may take any suitable shape, such as a helix, a coiled coil, or other configurations. Appropriate permeable materials from which the permeable gas collection portions may be formed may include Silastic® silicone rubber, available from Dow Corning (Midland, Mich.).

Figure 6:
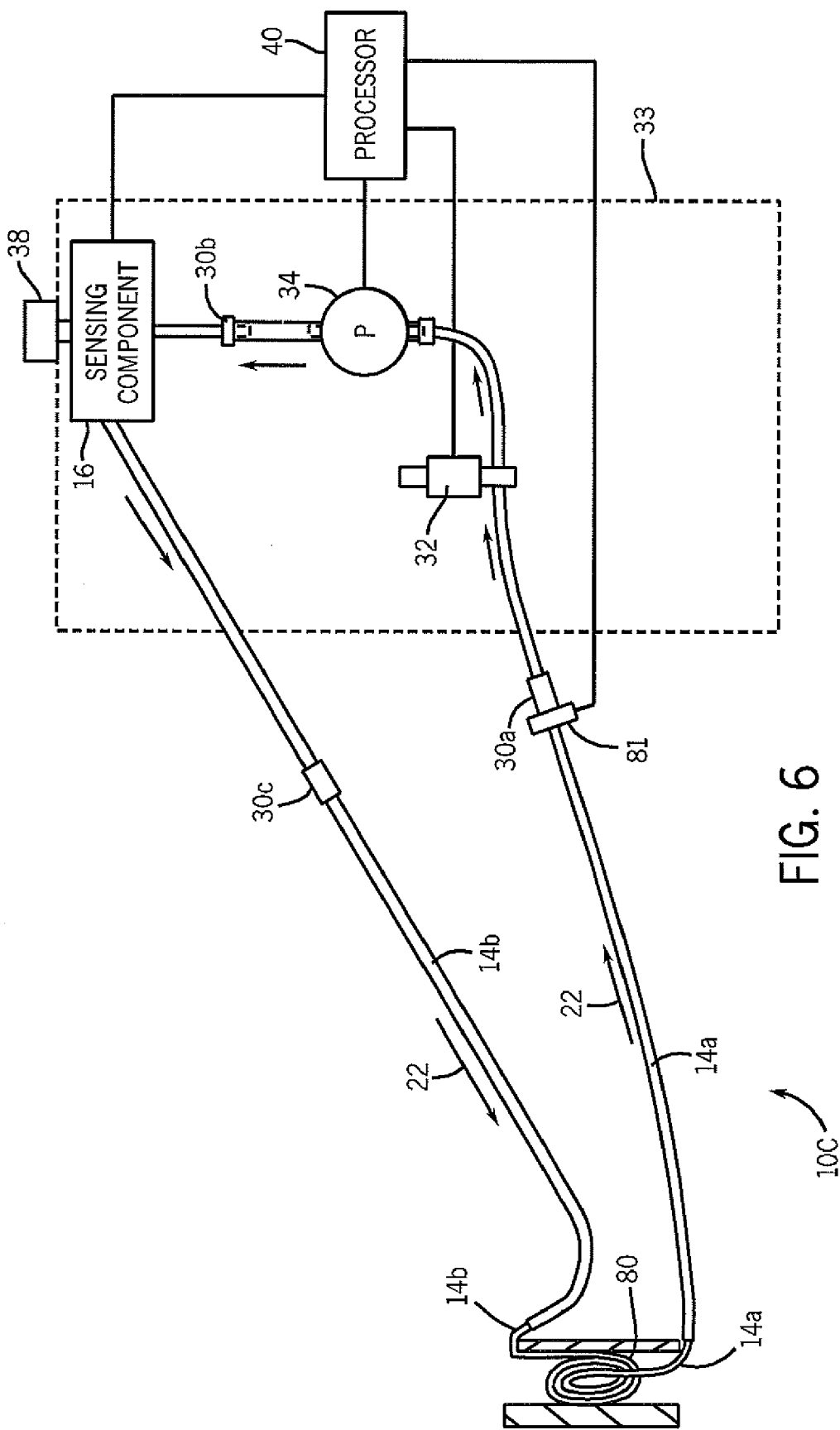
FIG. 6 illustrates a coiled tube that is permeable to a tissue constituent and that is connected to a pumping and sensing component system.

FIG. 6 illustrates a tissue constituent permeable coiled tube 80 connected to a pumping and sensing component system 33 by efferent conduit 14a and afferent conduit 14b. Efferent conduit 14a is adapted to draw the tissue constituent 22 to the sensing component 16. The system may include a calibration element 81 as described herein that is adapted to communicate with the processor 40 and provide information related to the characteristics of the disposable portion of the sensor 10D, which may include the tissue constituent permeable coiled tube 80 and certain segments of the conduit 14. It is envisioned that any suitable tissue constituent permeable assembly as described herein may be connected to the pumping and sensing component system 33 as shown.

Figure 7:
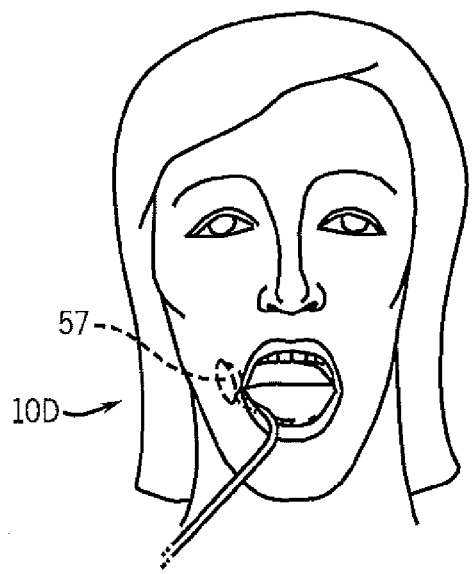
FIG. 7 illustrates a perspective view of a patient using a sensor including a barrier layer for detection of a physiological tissue constituent according to the present invention.
Figure 8:
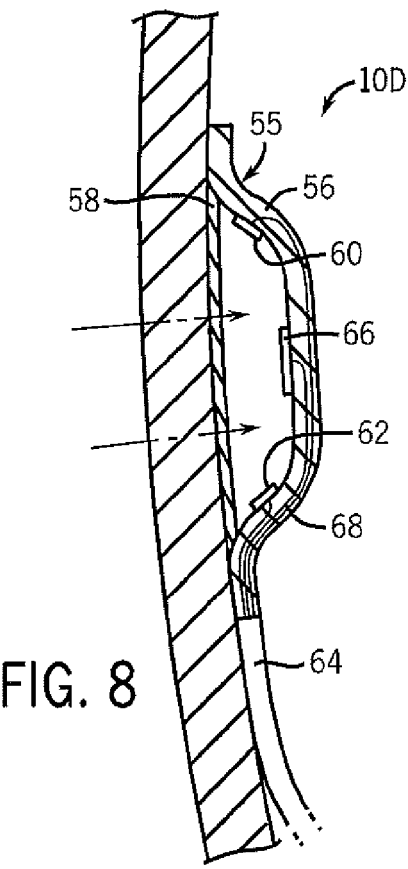
FIG. 8 is a schematic cross-sectional view of the sensor of FIG. 7.

The sensors as provided herein may prevent water infiltration into a sensing component by arranging a sensor such that the sensing component is removed from the tissue and thus is removed from bodily fluids. However, in certain embodiments it may be advantageous to provide a unitary sensor configuration including a gas collection chamber on which or within which the sensing component is disposed. Such an arrangement may be easier for a healthcare worker to apply and operate, as it does not involve a motive device. Additionally, such a sensor may be smaller and lighter, providing certain transportation and storage advantages. In such an embodiment, water infiltration into the sensor may be reduced by providing a sensor that includes a water barrier layer. FIG. 7-FIG. 8 illustrate an alternate embodiment of a tissue constituent sensor 10D in which the sensor body 55 includes a sensing component disposed proximate to a gas collection chamber 57. FIG. 7 shows the sensor applied to a patient. FIG. 8 shows a cross-sectional view of the sensor 10D. As depicted, water is prevented from infiltrating the sensor 10D by a barrier layer 58 as described herein that forms at least part of a surface of the sensor 10D that contacts the tissue. In an alternate embodiment (not shown), the sensor 10D may be configured to prevent water infiltration by a structure that absorbs and/or redirects water away from the sensing components. For example, the sensor 10B may include a water vapor permeable backflush tube that is selectively permeable to water vapor to allow water vapor to be absorbed and evaporate away from the sensing components without infiltrating the sensor. Such a tube may include a material such as Nafion (available from DuPont, Wilmington, Del.). The barrier layer 58 is connected to a housing 56 that, when applied to the mucosal tissue 28, forms a collection chamber that traps a tissue constituent 22 that diffuses through the barrier layer 58. It should be understood that the sensor 10D may include any sensing component as described herein. For example, sensing component may be an optical transducer. In such an embodiment, the trapped tissue constituent 22 may be irradiated by an emitter 60, and the emitted light that passes through the tissue constituent may be detected by a detector 62. The emitter 60 and the detector 62 are electrically coupled to a cable 64 by wires 68. The wavelength of the light emitted by the emitter 60 and the detection range of the detector 62 may be selected to detect a wide range of tissue constituents 22. For example, the emitter 60 may also include a filter, for example a 4.26 micron wavelength filter. Such a filter may be appropriate for use in an embodiment where carbon dioxide is measured.

In some embodiments, the sensor 10D is arranged to operate in transmission mode, and casings for the emitter and detector may be formed in the housing 56 on opposite sides of the sensor 10D. In an alternate embodiment, the emitter 60 and the detector 62 may be arranged to operate in reflectance mode (not shown), and can be located on the same side of sensor 10D. In such an embodiment (not shown), a mirror may be placed on the opposite side of the housing 56 to reflect the radiation emitted from the emitter 60 back to the detector 62. When employing optical sensing components 16, it may be advantageous to dispose an opaque or reflective layer on the tissue-contacting surface of the sensor 10D to prevent signal artifacts as a result of the absorption of a portion of the emitted light by the tissue 18.

In certain embodiments (not shown), the gas collection chamber 57 may include a calibration element 66 or other transducer that may provide a signal related to the volume and other characteristics of the gas collection chamber 57. Such a calibration element 66 may allow a downstream processor or monitor to determine a suitable amount of time to allow the sensor 10B to equilibrate (i.e. to allow the tissue constituent 22 to diffuse into the gas collection chamber 57) before obtaining accurate measurements related to the tissue constituent 22. Additionally, the calibration element 66 may be a coded resistor or EEPROM or any other suitable device as described herein that provides information related to the calibration of any optical sensing components. Such a calibration element 66 may be advantageous in increasing manufacturing yield of the sensor 10D. For example, a sensor 10D including such a calibration element 66 that provides information about the emission wavelength or wavelength range of the emitter 60 may be able to be more accurately calibrated for a wider range of potential emission wavelengths than a sensor lacking such a calibration element 66.

Figure 9:
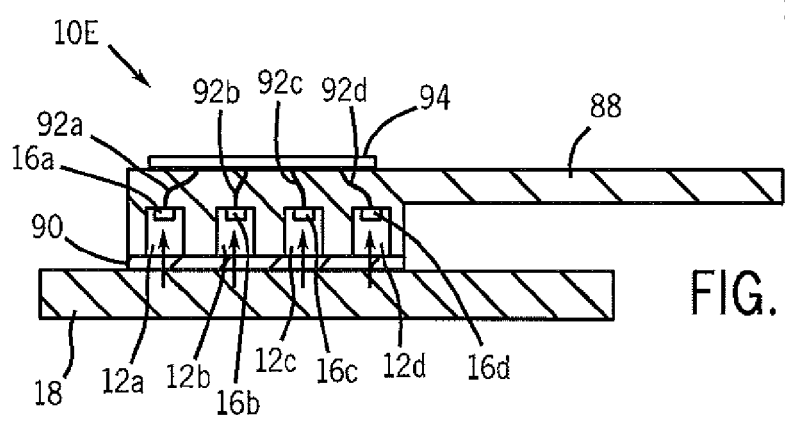
FIG. 9 is a sensor including multiple collection chambers for tissue constituent detection.
Figure 10:
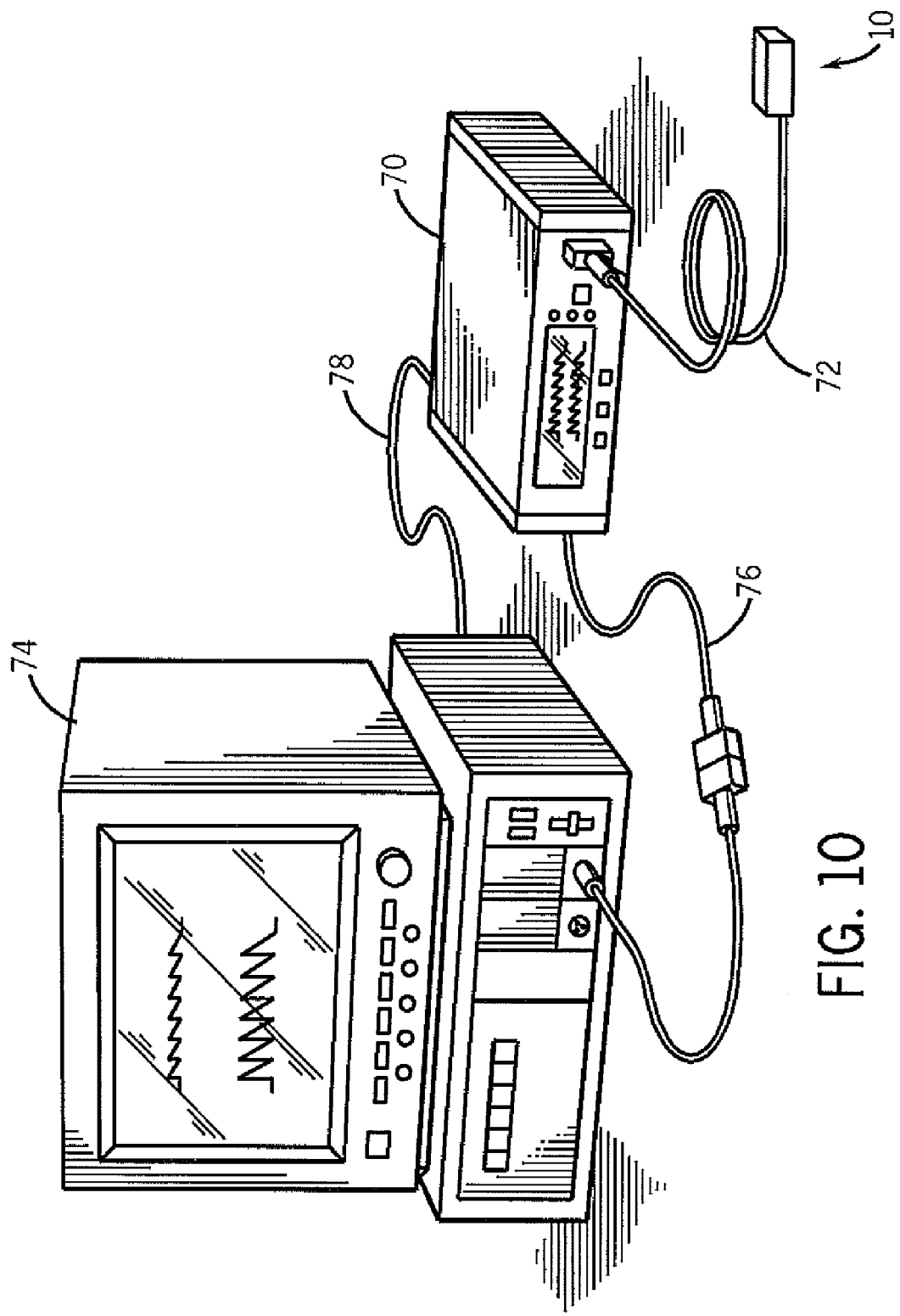
FIG. 10 illustrates a physiological constituent detection system coupled to a multi-parameter patient monitor and a sensor according to embodiments of the present invention.

It may be advantageous to provide a sensor 10E as a dipstick-like device with a holder 88 that has a familiar and comfortable shape that is easy to use. For example, water-resistant sensors as provided herein may be used in vivo by a patient much like an oral thermometer. FIG. 9 illustrates a cross-sectional view of a sensor assembly 10D according to the present techniques. Such a sensor 10E may be adapted to assess one or more tissue constituents 22, as illustrated. A barrier layer 90, as described herein, may reduce water infiltration into the sensor 10E. As illustrated, the sensor 10E includes multiple gas collection chambers, each of which may include a different sensing component 16. For example, sensing components 16a, 16b, 16c, and 16d may be adapted to each sense a different tissue constituent 22. In certain embodiments, the different tissue constituents may be carbon dioxide, carbon monoxide, oxygen, and other diffusible gases or volatile compounds. Each of the sensing components 16 may be electrically coupled to a display 94 by wires 92. The display may then indicate the concentrations of the tissue constituents 22 as measured by the sensing components 16. In an alternate embodiment, the sensor 10E may include electrical input and output wires (not shown) that may extend along the holder 88 to couple to a cable, which may be connected to a patient monitor. In another alternate embodiment (not shown), such a sensor 10F may be adapted to include distal sensing components 16 as described herein and a motive force structure to draw the tissue constituent 22 into the distal sensing components. Further, in another alternate embodiment (not shown), the barrier 90 may include a series of selectively permeable barriers specific for a variety of tissue constituents 22. Thus, each of the gas collection chambers 12 may only be permeable to a particular tissue constituent.

The sensor 10E may be inserted into the oral passage and placed adjacent to a mucosal tissue 18. The sensor 10E may be suitably sized and shaped such that a patient may easily close his or her mouth around the holder 88 with minimal discomfort. In certain embodiments, the sensor 10E may be adapted to be held against the cheek or any other mucosal tissue. The holder 88 may also include a handle portion that is accessible from outside the mouth and may be manipulated by the patient or a healthcare worker in order to properly position the sensor assembly 10E within the mouth.

Sensors as described herein may include any appropriate sensing component for assessing a tissue constituent, including chemical, electrical, optical, non-optical, quantum-restricted, electrochemical, enzymatic, spectrophotometric, fluorescent, or chemiluminescent indicators or transducers. In certain embodiments, the sensing component may include optical components, e.g., an emitter and detector pair that may be of any suitable type. For example, the emitter may be one or more light emitting diodes adapted to transmit one or more wavelengths of light in the red to infrared range, and the detector may one or more photodetectors selected to receive light in the range or ranges emitted from the emitter. Alternatively, an emitter may also be a laser diode or a vertical cavity surface emitting laser (VCSEL). An emitter and detector may also include optical fiber sensing components. An emitter may include a broadband or "white light" source, in which case the detector could include any of a variety of elements for selecting specific wavelengths, for example reflective or refractive elements or interferometers. These kinds of emitters and/or detectors would typically be coupled to the rigid or rigidified sensor via fiber optics. Alternatively, a sensor may sense light detected from the tissue is at a different wavelength from the light emitted into the tissue. Such sensors may be adapted to sense fluorescence, phosphorescence, Raman scattering, Rayleigh scattering and multi-photon events or photoacoustic effects. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

Alternatively, the sensing component may include an active ingredient of the indicating element, for example the active ingredient involved in providing the required response signal when exposed to a given concentration of carbon dioxide or other constituents. The active ingredient may be any indicator that is sensitive to the presence of carbon dioxide and that is capable of being calibrated to give a response signal corresponding to a given predetermined concentration of carbon dioxide. The signal may be visual, e.g. a change in color, or electrical. Indicators which provide a color change in a presence of carbon dioxide may include chromogenic pH-sensitive indicators and oxidation/reduction indicators.

A chromogenic pH-sensitive indicator may provide a color change upon exposure to a given concentration of carbon dioxide or other metabolites in the presence of other ingredients of the element that provide the appropriate chemical conditions to induce the required color change. For such an indicator to be capable of giving a determination of carbon dioxide, it is typically used in combination with a suitable base that provides an alkaline solution. The hydroxyl ions or amine residues present in the alkaline solution react chemically with carbon dioxide to produce a carbonate, bicarbonate and/or carbamate moiety. The resulting reaction depletes the hydroxyl ion or amine at the interface and thus lowers the pH at the surface of the component impregnated with the indicating element. The lowering of the pH causes a color change in the indicator.

Chromogenic pH-sensitive indicators according to the present techniques may include metacresol purple, thymol blue, cresol red, phenol red, xylenol blue, a 3:1 mixture of cresol red and thymol blue, bromthymol blue, neutral red, phenolphthalein, rosolic acid, alpha-naphtholphthalein and orange I. Examples of other indicators which may be used include bromcresol purple, bromphenol red, p-nitrophenol, m-nitrophenol, curcumin, quinoline blue, thymolphthalein and mixtures thereof. Suitable bases include sodium carbonate, lithium hydroxide, sodium hydroxide, potassium hydroxide, potassium carbonate, sodium barbitol, tribasic sodium phosphate, dibasic sodium phosphate, potassium acetate, monoethanolamine, diethanolamine and piperidine.

The sensing component may include a semi-conductive sensing element, such as an ion-sensitive field-effect transistor (ISFET). An ISFET may include a silicon dioxide gate for a pH selective membrane. Such a sensor may be adapted to sense downstream changes in hydrogen ion concentration in response to changes in carbon dioxide or other tissue constituent concentrations.

The sensing component may also include an enzyme-based detection system. For example, one such enzyme may be carbonic anhydrase, which is an enzyme that assists interconversion of carbon dioxide and water into carbonic acid, protons, and bicarbonate ions. As described above, this reaction lowers the pH at the surface of the component impregnated with the indicating element. The lowering of the pH may cause a color change in the indicator. Another such enzyme-based detection system is an enzyme linked immunosorbent assay (ELISA). For example, such an assay may be appropriate when assessing tissue proteins. Thus, the indicator element may include a primary antibody specific for the tissue protein of interest, and a labeled secondary binding ligand or antibody, or a secondary binding ligand or antibody in conjunction with a labeled tertiary antibody or third binding ligand. The label may be an enzyme that will generate color development upon incubating with an appropriate chromogenic substrate. Suitable enzymes include urease, glucose oxidase, alkaline phosphatase or hydrogen peroxidase.

A chemical indicator may be used in conjunction with an electrical or electronic device that is adapted to detect and measure changes in the ambient chemical parameters induced by the presence of critical amounts of carbon dioxide. For example, optical fiber carbon dioxide sensors may be used to convert a change in a chemical indicator to a quantitative measurement of carbon dioxide in the sample Generally, such sensors operate by directing light of a predetermined wavelength from an external source through the optical fiber to impinge the chemical indicator. The intensity of the emitted fluorescent light returning along the fiber is directly related to the concentration of carbon dioxide in the sample, as a result of the pH-sensitive indicator material present at the fiber tip (i.e., the pH of the indicator solution is directly related to carbon dioxide concentration, as a result of carbonic acid formation). The emitted light is carried by the optical fiber to a device where it is detected and converted electronically to a carbon dioxide concentration value. The sensor may additionally have a reference dye present in the indicator composition. The intensity of the light emitted form the reference dye may be used to compensate, via rationing, the signal obtained from the indicator. Other components may be incorporated into the indicator composition including surfactants, antioxidants and ultraviolet stabilizers may also be present in the indicator composition. The sensing component may be formed from any appropriate substrate. For example, the sensing component may be filter paper, which may be soaked in, dipped in, or otherwise exposed to the appropriate carbon dioxide-sensing compounds. In certain embodiments, the filter paper may be dipped into a solution containing the indicating compounds on only one side. The sensing component may also be polysulfone, polypropylene, or other polymer substrates. The sensing component may be a thin film, or a thicker substrate. A thicker substrate may lead to a slower response time, which may be advantageous in situations in which a sensor is monitoring carbon dioxide levels over a longer period of time. Additionally, the sensing component may have pores of a variety of sizes.

The sensing component may include an electrochemical transducer, which may be adapted to detect and measure changes in ambient chemical parameters induced by the presence of critical amounts of a tissue constituent. In one embodiment, the sensing component may include a sensor that employs cyclic voltammetry for carbon dioxide detection. Such sensors are available from Giner, Inc., Newton, Mass. For example, the sensing component may be a thick film catalyst sensor utilizing a proton exchange membrane. Such a sensing component may include thick film screen printed electrodes and an electrochemically reversible metal oxide catalysts. Appropriate catalysts include MO, $M_2O_3$, $MO_2$, where M is a metal that is any suitable metal, including platinum ruthenium or iridium. Generally, such sensors operate by sensing chemical reactions caused by proton dissociation from water in which carbon dioxide is dissolved. Dissociated water protons may electrochemically reduce a metal oxide layer of the sensor. The electrochemical reduction of the metal oxide will result in generation of an electrical current, which varies in response to the degree of electrochemical reduction.

In another embodiment, the sensing component may include an artificial nose assembly. In such an embodiment, the tissue constituents may contact an array of electrodes coated with polymers that have characteristic electrical properties. The polymers change electrical resistance when contacted with specific volatile materials.

In another embodiment, the sensing component may include quantum-restricted components, including carbon nanotubes, buckeyballs, or quantum dots. Generally, quantum-restricted components may be coated or otherwise modified with a compound that is sensitive to the tissue constituent of interest. Interaction of the tissue constituent with the compound may affect the electrical properties of the quantum-restricted components such that an electrical feedback may result. In one such example, carbon nanotubes may be coated with a carbon dioxide-sensitive compound or polymer, such as a polyethyleneimine and starch polymer. Carbon dioxide may combine with primary and tertiary amines in the polyethyleneimine and starch polymer coating to form carbamates. The chemical reaction lowers the pH of the polymer coating, altering charge transfer to the carbon nanotubes and resulting in an electrical signal proportional to the pH change. Other suitable polymer coatings may be adapted to sense other tissue constituents of interest, such as oxygen or carbon monoxide. In other embodiments, the quantum-restricted component may include a binding molecule, such as a receptor or an enzyme that is specific for the tissue constituent of interest. One such molecule may include carbonic anhydrase. Binding of the tissue constituent to its receptor may affect a downstream response that may result in a change in the electrical properties of a quantum-restricted component.

The exemplary sensors, described here generically as a sensor 10, may be coupled to a monitor 70 that may display the concentration of tissue constituents as shown in FIG. 8. It should be appreciated that the cable 72 of the sensor 10 may be coupled to the monitor 70 or it may be coupled to a transmission device (not shown) to facilitate wireless transmission between the sensor 10 and the monitor 70. The monitor 70 may be any suitable monitor 70, such as those available from Nellcor Puritan Bennett, Inc. Furthermore, to upgrade conventional tissue constituent detection provided by the monitor 70 to provide additional functions, the monitor 70 may be coupled to a multi-parameter patient monitor 74 via a cable 74 connected to a sensor input port or via a cable 76 connected to a digital communication port.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of carbon dioxide, but these techniques may also be utilized for the measurement and/or analysis of other tissue and/or blood constituents. Rather, the invention is to cover all modifications, equivalents, and alternatives falling within the spirit and scope of the invention as defined by the following appended claims. It will be appreciated by those working in the art that sensors fabricated using the presently disclosed and claimed techniques may be used in a wide variety of contexts. That is, while the invention has primarily been described in conjunction with the measurement of carbon dioxide concentration in blood, the sensors fabricated using the present method may be used to evaluate any number of sample types in a variety of industries, including fermentation technology, cell culture, and other biotechnology applications.

What is claimed is:

1. A system comprising:
    a coiled conduit permeable to a tissue constituent, wherein the coiled conduit is adapted to be placed in direct contact with a tissue;
    an efferent conduit in fluid communication with the coiled conduit, wherein the efferent conduit is adapted to transfer the tissue constituent from the coiled conduit to at least one sensing component, wherein the sensing component is adapted to provide a signal related to the tissue constituent;
    an afferent conduit adapted to transfer the tissue constituent from the sensing component to the coiled conduit; and
    a motive force structure adapted circulate the tissue constituent through the system, wherein the motive force structure is adapted to be operatively connected to at least one of the efferent conduit, the afferent conduit, or the sensing component.

2. The system, as set forth in claim 1, wherein the tissue constituent comprises carbon dioxide, oxygen, ethanol, or carbon monoxide.

3. The system, as set forth in claim 1, wherein the tissue constituent comprises a volatile anesthetic agent, a volatile product of metabolism, or a volatile xenobiotic.

4. The system, as set forth in claim 1, comprising a barrier layer disposed on at least part of a surface of the coiled conduit, wherein the barrier layer is substantially impermeable to water.

5. The system, as set forth in claim 1, comprising a barrier layer defining at least part of a surface of the coiled conduit, wherein the barrier layer is selectively permeable to the tissue constituent.

6. The system, as set forth in claim 1, wherein the sensing component comprises at least one of a non-optical transducer, an optical transducer, a chemical indicator, a spectroscopic transducer, or an electrochemical transducer.

7. The system, as set forth in claim 1, wherein the motive force structure comprises at least one of a pump, a one-way valve, a kinetic motion structure, or a piezoelectrically powered structure.

8. The system, as set forth in claim 1, comprising an agent adapted to be placed proximate to the tissue, wherein the agent is adapted to increase blood flow to the tissue or wherein the agent is adapted to increase the tissue's permeability to the tissue constituent.

9. The system, as set forth in claim 8, wherein the agent comprises an electrical heating element, a chemical heating element, nicotinic acid, or salicylic acid.

10. A sensor comprising:
    a gas collection structure comprising a coiled tube or a folded tube, wherein the coiled or folded tube is at least partially permeable to a tissue constituent, and wherein the coiled or folded tube is adapted to be placed in direct contact with the tissue; and
    an efferent conduit adapted to transfer the tissue constituent from the gas collection structure to a sensing component, wherein the sensing component is adapted to provide a signal related to the tissue constituent; and
    an afferent conduit adapted to transfer the tissue constituent from the sensing component to the gas collection structure.

11. The sensor, as set forth in claim 10, wherein the tissue constituent comprises carbon dioxide, oxygen, ethanol, or carbon monoxide.

12. The sensor, as set forth in claim 10, wherein the tissue constituent comprises a volatile anesthetic agent, a volatile product of metabolism, or a volatile xenobiotic.

13. The sensor, as set forth in claim 10, wherein the coiled tube is coiled in a substantially flat configuration.

14. The sensor, as set forth in claim 10, wherein the folded tube is folded in a substantially zigzag configuration.

15. The sensor, as set forth in claim 10, wherein the coiled tube or the folded tube is partially coated with a material that is impermeable to the tissue constituent.

* * * * *